United States Patent
Yamashita et al.

(10) Patent No.: US 9,568,422 B2
(45) Date of Patent: Feb. 14, 2017

(54) LIGHT BEAM INCIDENT DEVICE AND REFLECTED LIGHT MEASUREMENT DEVICE

(71) Applicant: ADVANTEST CORPORATION, Tokyo (JP)

(72) Inventors: Tomoyu Yamashita, Miyagi (JP); Akiyoshi Irisawa, Miyagi (JP)

(73) Assignee: ADVANTEST CORPORATION, Tokyo (JP)

( * ) Notice: Subject to any disclaimer, the term of this patent is extended or adjusted under 35 U.S.C. 154(b) by 224 days.

(21) Appl. No.: 13/783,549

(22) Filed: Mar. 4, 2013

(65) Prior Publication Data

US 2014/0168652 A1 Jun. 19, 2014

Related U.S. Application Data

(60) Provisional application No. 61/737,991, filed on Dec. 17, 2012.

(51) Int. Cl.
*G02B 17/00* (2006.01)
*G01N 21/55* (2014.01)
*G01N 21/3581* (2014.01)

(52) U.S. Cl.
CPC .......... *G01N 21/55* (2013.01); *G01N 21/3581* (2013.01)

(58) Field of Classification Search
CPC .............. G01N 21/211; G01N 21/3581; G01N 21/3586; G01N 21/01; G01N 21/55; G01B 11/00; G01B 11/02; G01B 11/06; G01B 11/24; G02B 26/0816
See application file for complete search history.

(56) References Cited

U.S. PATENT DOCUMENTS

| | | | |
|---|---|---|---|
| 6,288,841 B1 * | 9/2001 | Lee et al. .................... | 359/618 |
| 2002/0101585 A1 | 8/2002 | Benesch et al. | |
| 2006/0164642 A1 * | 7/2006 | Amary et al. ............. | 356/369 |
| 2007/0235650 A1 * | 10/2007 | Federici .................. | G01J 3/42 |
| | | | 250/341.8 |

(Continued)

FOREIGN PATENT DOCUMENTS

| | | |
|---|---|---|
| JP | 2002-540422 | 11/2002 |
| JP | 2003-005238 | 1/2003 |

(Continued)

OTHER PUBLICATIONS

Japanese Office Action mailed Jun. 25, 2015 in Japanese Patent Application No. 2013-193742.

*Primary Examiner* — Alicia M Harrington
(74) *Attorney, Agent, or Firm* — Greenblum & Bernstein, P.L.C.

(57) ABSTRACT

Provided is a light beam incident device including an off-axis parabolic mirror that receives parallel light beams and converges the parallel light beams at one point on an object to be measured, and an incident-side light reception surface of a mirror that feeds the parallel light beams to the off-axis parabolic mirror. An angle (incident angle) between the object to be measured and converged light beams obtained by converging the parallel light beams changes in accordance with a light reception portion at which the off-axis parabolic mirror receives the parallel light beams. The incident side light reception surface of the mirror can change the light reception portion by moving with respect to the off-axis parabolic mirror.

9 Claims, 4 Drawing Sheets

A case where a mirror 12 is moved downward
(a)

A case where a mirror 12 is moved upward
(b)

(56) References Cited

U.S. PATENT DOCUMENTS

2010/0053627 A1    3/2010  Shyu et al.
2010/0059677 A1*   3/2010  Leonhardt ................ G02B 3/04
                                                           250/330
2012/0286797 A1    11/2012 Kato et al.

FOREIGN PATENT DOCUMENTS

| JP | 2010-060543 | 3/2010 |
| JP | 2010-217473 | 9/2010 |
| JP | 2012-237657 | 12/2012 |
| WO | 2010/106589 | 9/2010 |

* cited by examiner

A case where a mirror 12 is moved downward (a)

A case where a mirror 12 is moved upward (b)

A case where a mirror 12 is moved downward (a)

A case where a mirror 12 is moved upward (b)

A case where a mirror 12 is moved downward (a)

A case where a mirror 12 is moved upward (b)

LIGHT BEAM INCIDENT DEVICE AND REFLECTED LIGHT MEASUREMENT DEVICE

BACKGROUND ART

1. Technical Field of the Invention

The present invention relates to light irradiation onto an object to be measured.

2. Related Art

FIG. 4 shows an optical system of a conventional reflection measurement device which measures optical characteristics of a flat-shape sample. A description will now be given for the case where terahertz waves (electromagnetic waves having a frequency of 0.01 THz-10 THz) are measuring light, as an example. The terahertz waves output from a terahertz wave generator are reflected by an off-axial parabolic mirror, resulting in condensed terahertz waves. The terahertz waves are reflected by a flat surface mirror on the way, and are condensed on a sample surface. The terahertz waves reflected by the sample surface are again reflected by the flat surface mirror, are formed into collimated terahertz waves by an off-axis parabolic mirror, and are input into a terahertz detector.

For measuring the optical characteristics of a thin film or film as a sample, the measurement may be carried out while an incident angle θ of the measuring light entering the sample is changed. This is because, for example, the refractive index of the sample can be calculated highly precisely by acquiring the optical characteristics at various incident angles.

There is known a technique of irradiating a specimen with terahertz waves and detecting the reflected terahertz waves reflected by the respective layers (refer to the Abstract of JP 2012-237657 A, for example).

SUMMARY OF THE INVENTION

On this occasion, for measuring an incident angle (θ) dependency of an optical characteristic of the sample, it is necessary to detect the terahertz waves reflected on the sample for various values of the incident angle (θ).

However, the incident angle (θ) is constant according to the related art shown in FIG. 4. In order to change the value of the incident angle (θ), an angle of a tilted surface of a flat surface mirror with respect to the incident light needs to be changed, accordingly. In order to do so, the flat surface mirror itself needs to be replaced, which requires a large amount of labor.

It is therefore an object of the present invention to enable a readily change of a light incident angle to a sample.

According to the present invention, a light beam incident device includes: a light beam converging device that receives parallel light beams, and converges the parallel light beams at one point on an object to be measured; and a light beam feeding device that feeds the parallel light beams to the light beam converging device, wherein: an angle between the object to be measured and converged light beams obtained by converging the parallel light beams changes in accordance with a light reception portion at which the light beam converging device receives the parallel light beams; and the light beam feeding device is capable of changing the light reception portion.

According to the thus constructed light beam incident device, a light beam converging device receives parallel light beams, and converges the parallel light beams at one point on an object to be measured. A light beam feeding device feeds the parallel light beams to the light beam converging device. An angle between the object to be measured and converged light beams obtained by converging the parallel light beams changes in accordance with a light reception portion at which the light beam converging device receives the parallel light beams. The light beam feeding device is capable of changing the light reception portion.

According to the present invention, the light beam incident device may include a paralleling device that changes travel directions of reflected light beams obtained by reflecting the converged light beams at the one point, thereby obtaining reflected parallel light beams traveling in parallel.

According to the light beam incident device of the present invention, the light beam converging device and the paralleling device may be unified with each other.

According to the light beam incident device of the present invention, the light beam converging device and the paralleling device may be independent from each other.

According to the light beam incident device of the present invention, the light beam converging device may be any one of an off-axis parabolic mirror and an aspherical lens.

According to the light beam incident device of the present invention, the light beam feeding device may receive the incident light beams travelling in parallel and change the travel direction by the right angle, thereby obtaining the parallel light beams.

According to the light beam incident device of the present invention, the light beam feeding device may be capable of changing the light reception portion by moving with respect to the light beam converging device.

According to the present invention, the light beam incident device may include a travel direction changing device that receives the reflected parallel light beams, and changes the travel direction thereof by the right angle, thereby obtaining light beams with a changed travel direction.

According to the light beam incident device of the present invention, the light beam feeding device may receive the incident light beams travelling in parallel and changes the travel direction thereof by the right angle, thereby obtaining the parallel light beams; and the travel direction of the incident light beams and the travel direction of the light beams with a changed travel direction may be the same.

According to the light beam incident device of the present invention, the light beam feeding device and the travel direction changing device may be unified with each other.

According to the present invention, a reflected light measurement device includes: the light beam incident device according to the present invention; a light source that feeds the incident light beams to the light beam incident device; and a detector that detects the light beams with a changed travel direction.

MODES FOR CARRYING OUT THE INVENTION

A description will now be given of an embodiment of the present invention referring to drawings.

Figure 1:
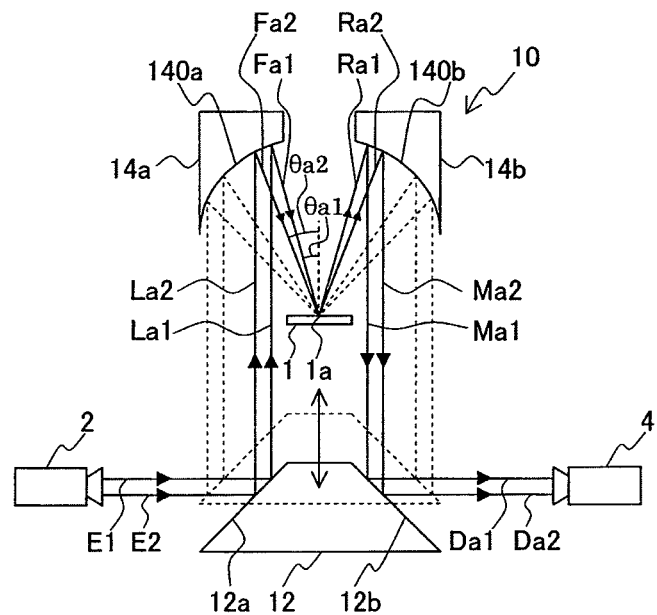
FIG. 1 is a front view showing a configuration of a reflected light measurement device according to an embodiment of the present invention, and shows a case where a mirror 12 is moved downward (refer to FIG. 1(*a*)) and a case where the mirror 12 is moved upward (refer to FIG. 1(*b*))
Figure 1:
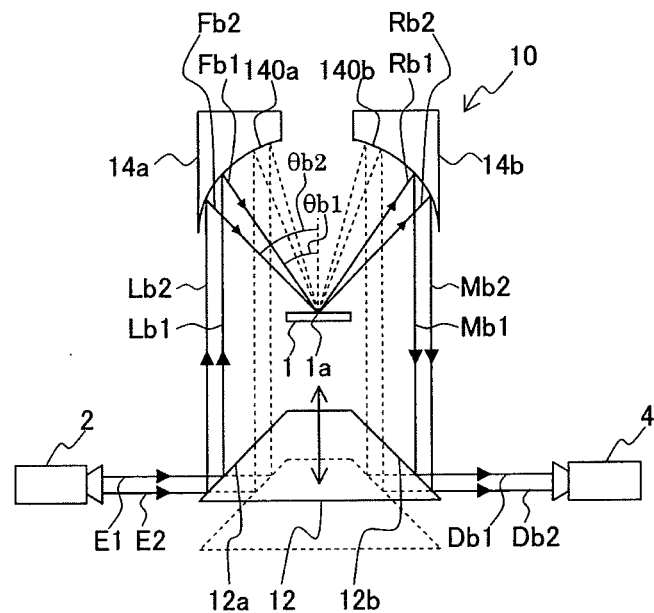

FIG. 1 is a front view showing a configuration of a reflected light measurement device according to an embodiment of the present invention, and shows a case where a mirror 12 is moved downward (refer to FIG. 1(a)) and a case where the mirror 12 is moved upward (refer to FIG. 1(b)).

The reflected light measurement device according to an embodiment of the present invention includes a light beam incident device 10, a light source 2, and a detector 4.

The light source 2 provides (a mirror 12 of) the light beam incident device 10 with incident light beams E1 and E2. Terahertz waves (electromagnetic waves having frequencies of 0.01 THz-10 THz), for example, are assumed as the incident light beams E1 and E2. Beams of the terahertz wave are output from the light source 2, and contours of the beams on the page of FIG. 1 are illustrated as the incident light beams E1 and E2 for the sake of illustration. It should be noted that the beams are collimated, and the incident light beams E1 and E2 travel in parallel to each other.

The detector 4 detects detected light beams (light beams with a changed travel direction) Da1 and Da2 (or Db1 and Db2). As a result, characteristics (such as optical characteristics and refractive index) of an object to be measured 1 can be measured. The object to be measured 1 may be a thin film or a film such as an antireflection film, a protection film, and a transparent electrically conductive film, for example. Refer to FIG. 1(a) for the detected light beams Da1 and Da2, and refer to FIG. 1(b) for the detected light beams Db1 and Db2.

The light beam incident device 10 is provided with the mirror (a light beam feeding device and a travel direction changing device) 12, an off-axis parabolic mirror (light beam converging device) 14a, and an off-axis parabolic mirror (paralleling device) 14b. It should be noted that the off-axis parabolic mirror (light beam converging device) 14a and the off-axis parabolic mirror (paralleling device) 14b are independent from each other.

The mirror 12 includes an incident-side light reception surface (light beam feeding device) 12a, and an emission-side light reception surface (travel direction changing device) 12b. Although the incident-side light reception surface (light beam feeding device) 12a and the emission-side light reception surface (travel direction changing device) 12b may be surfaces on independent members; they are unified and are surfaces on the same member (mirror 12), according to an embodiment of the present invention.

The incident-side light reception surface (light beam feeding device) 12a is a flat surface inclined by 45 degrees with respect to the incident light beams E1 and E2, and is a surface that reflects the incident light beams E1 and E2. The incident-side light reception surface (light beam feeding device) 12a receives and reflects the incident light beams E1 and E2 travelling in parallel from the light source 2, and changes the travel direction by the right angle. The light beams E1 and E2 of which travel direction has been changed by the right angle are referred to as parallel light beams La1 and La2 (or Lb1 and Lb2), respectively. The incident light beam E1 is reflected by the incident-side light reception surface 12a and becomes the parallel light beam La1 (or Lb1). The incident light beam E2 is reflected by the incident-side light reception surface 12a and becomes the parallel light beam La2 (or Lb2). Refer to FIG. 1(a) for the parallel light beams La1 and La2, and refer to FIG. 1(b) for the parallel light beams Lb1 and Lb2.

The parallel light beams L1 and L2 travel toward the off-axis parabolic mirror (light beam converging device) 14a. Namely, the incident-side light reception surface (light beam feeding device) 12a feeds the parallel light beams La1 and La2 (or Lb1 and Lb2) to the off-axis parabolic mirror (light beam converging device) 14a.

The off-axis parabolic mirror (light beam converging device) 14a receives the parallel light beams La1 and La2 (or Lb1 and Lb2), thereby converging the parallel light beams La1 and La2 (or Lb1 and Lb2) at one point 1a on the surface of the object to be measured 1. The off-axis parabolic mirror 14a includes a reflective parabolic surface 140a, and receives and reflects the parallel light beams La1 and La2 (or Lb1 and Lb2) on the reflective parabolic surface 140a. The one point 1a on the surface of the object to be measured 1 is arranged at the focal point of the reflective parabolic surface 140a.

Although, according to an embodiment of the present invention, the one point 1a is on the surface of the object to be measured 1, the one point 1a may be inside the object to be measured 1.

On this occasion, light beams that is obtained by converging the parallel light beams La1 and La2 (or Lb1 and Lb2) with the off-axis parabolic mirror 14a are referred to as converged light beams Fa1 and Fa2 (or Fb1 and Fb2).

Respective angles between the object to be measured 1 and the converged light beams Fa1 and Fa2 (or Fb1 and Fb2) (such as incident angles θa1 and θa2 (or θb1 and θb2) of the converged light beams to the object to be measured 1) change in accordance with light reception portions at which the off-axis parabolic mirror (light beam converging device) 14a receives the parallel light beams La1 and La2 (or Lb1 and Lb2).

For example, referring to FIG. 1(a), if the mirror 12 is moved downward, the light reception portions are on the right end side of the reflective parabolic surface 140a. In this case, the incident angles of the converged light beams Fa1 and Fa2 to the object to be measured 1 are θa1 and θa2, respectively.

Moreover, referring to FIG. 1(b), if the mirror 12 is moved upward, the light reception portions are on the left end side of the reflective parabolic surface 140a. In this case, the incident angles of the converged light beams Fb1 and Fb2 to the object to be measured 1 are θb1 and θb2, respectively. It should be noted that θa1, θa2, θb1, and θb2 are different from each other. For example, θb2>θb1>θa2>θa1.

As described above, the incident-side light reception surface (light beam feeding device) 12a of the mirror 12 can move upward and downward in the travel direction of the parallel light beams La1 and La2 (and Lb1 and Lb2) with respect to the off-axis parabolic mirror (light beam converging device) 14a (the incident-side light reception surface 12a can move along an up-down arrow near the mirror 12 in FIG. 1), thereby changing the light reception portions on the reflective parabolic surface 140a.

It should be noted that the mirror 12 is not necessarily arranged only at the two locations illustrated in FIG. 1(a)

and FIG. 1(b). For example, the mirror 12 may be arranged at an arbitrary position between the position illustrated in FIG. 1(a) and the position illustrated in FIG. 1(b). If the mirror 12 is moved finely and continuously from the position illustrated in FIG. 1(a) to the position illustrated in FIG. 1(b) (or from the position illustrated in FIG. 1(b) to the position illustrated in FIG. 1(a)), the light reception portion on the reflective parabolic surface 140a can be changed finely and continuously.

The converged light beams Fa1 and Fa2 (or Fb1 and Fb2) are reflected at the one point 1a on the surface of the object to be measured 1. The reflected light beams are referred to as reflected light beams Ra1 and Ra2 (or Rb1 and Rb2).

The off-axis parabolic mirror (paralleling device) 14b includes a reflective parabolic surface 140b, and receives and reflects the reflected light beams Ra1 and Ra2 (or Rb1 and Rb2) on the reflective parabolic surface 140b. The one point 1a on the surface of the object to be measured 1 is arranged at the focal point of the reflective parabolic surface 140b.

The off-axis parabolic mirror (paralleling device) 14b changes the travel directions of the reflected light beams Ra1 and Ra2 (or Rb1 and Rb2) thereby obtaining light beams travelling in parallel. The light beams obtained by the off-axis parabolic mirror 14b changing the travel directions of the reflected light beams Ra1 and Ra2 (or Rb1 and Rb2) to be parallel are referred to as reflected parallel light beams Ma1 and Ma2 (or Mb1 and Mb2).

The emission-side light reception surface (travel direction changing device) 12b is a flat surface inclined by 45 degrees with respect to the reflected parallel light beams Ma1 and Ma2 (and Mb1 and Mb2), and a surface that reflects the reflected parallel light beams Ma1 and Ma2 (and Mb1 and Mb2). The emission-side light reception surface (travel direction changing device) 12b receives and reflects the reflected parallel light beams Ma1 and Ma2 (or Mb1 and Mb2), thereby changing the travel direction by the right angle. The light beams obtained by changing, by the right angle, the travel direction of the reflected parallel light beams Ma1 and Ma2 (or Mb1 and Mb2) are referred to as light beams with a changed travel direction Da1 and Da2 (or Db1 and Db2).

It should be noted that the travel direction of the incident light beams E1 and E2 and the travel direction of the light beams with a changed travel direction Da1 and Da2 (and Db1 and Db2) are the same. For example, as illustrated in FIG. 1, the light beams with a changed travel direction Da1 and Da2 (and Db1 and Db2) exist on the extensions of the incident light beams E1 and E2. Moreover, for example, even if the light beams with a changed travel direction Da1 and Da2 (and Db1 and Db2) do not exist on the extensions of the incident light beams E1 and E2, as long as the incident light beams E1 and E2 and the light beams with a changed travel direction Da1 and Da2 (and Db1 and Db2) are parallel to each other, it is considered that these beams "travel in the same direction".

A description will now be given of an operation of an embodiment of the present invention.

First, referring to FIG. 1(a), the case where the mirror 12 is moved downward is considered. In this case, the collimated beams of the terahertz wave are output from the light source 2, and the incident light beams E1 and E2 parallel to each other are fed to the incident-side light reception surface 12a.

The incident light beams E1 and E2 are reflected by the incident-side light reception surface 12a, the travel direction thereof is changed by the right angle, and become the parallel light beams La1 and La2. The parallel light beams La1 and La2 are fed on the right end side of the reflective parabolic surface 140a of the off-axis parabolic mirror 14a.

The parallel light beams La1 and La2 hit on the right end side of the reflective parabolic surface 140a of the off-axis parabolic mirror 14a, are reflected, and converge at the one point 1a on the surface of the object to be measured 1 arranged at the focal point of the reflective parabolic surface 140a (refer to the converged light beams Fa1 and Fa2). On this occasion, the incident angles of the converged light beams Fa1 and Fa2 onto the object to be measured 1 are $\theta a1$ and $\theta a2$, respectively.

The converged light beams Fa1 and Fa2 are reflected at the one point 1a on the surface of the object to be measured 1, become the reflected light beams Ra1 and Ra2, hit on the reflective parabolic surface 140b of the off-axis parabolic mirror 14b, and become the reflected parallel light beams Ma1 and Ma2.

The reflected parallel light beams Ma1 and Ma2 are reflected by the emission-side light reception surface 12b, the travel direction thereof is changed in the travel direction by the right angle, and become the light beams with a changed travel direction Da1 and Da2.

The light beams with a changed travel direction Da1 and Da2 are detected by the detector 4.

Then, referring to FIG. 1(b), the case where the mirror 12 is moved upward is considered. In this case, the beams of the terahertz wave are output from the light source 2, and the incident light beams E1 and E2 parallel to each other are fed to the incident-side light reception surface 12a.

The incident light beams E1 and E2 are reflected by the incident-side light reception surface 12a, the travel direction thereof is changed by the right angle, and become the parallel light beams Lb1 and Lb2. The parallel light beams Lb1 and Lb2 are fed on the left end side of the reflective parabolic surface 140b of the off-axis parabolic mirror 14b.

The parallel light beams Lb1 and Lb2 hit on the left end side of the reflective parabolic surface 140b of the off-axis parabolic mirror 14b, are reflected, and converge at the one point 1a on the surface of the object to be measured 1 arranged at the focal point of the reflective parabolic surface 140b (refer to converged light beams Fb1 and Fb2). On this occasion, the incident angles of the converged light beams Fb1 and Fb2 to the object to be measured 1 are $\theta b1$ and $\theta b2$, respectively. It should be noted that $\theta b2 > \theta b1 > \theta a2 > \theta a1$.

The converged light beams Fb1 and Fb2 are reflected at the one point 1a on the surface of the object to be measured 1, become the reflected light beams Rb1 and Rb2, hit on the reflective parabolic surface 140b of the off-axis parabolic mirror 14b, and become the reflected parallel light beams Mb1 and Mb2.

The reflected parallel light beams Mb1 and Mb2 are reflected by the emission-side light reception surface 12b, the travel direction thereof is changed by the right angle, and become the light beams with a changed travel direction Db1 and Db2.

The light beams with a changed travel direction Db1 and Db2 are detected by the detector 4.

According to an embodiment of the present invention, since the incident angles $\theta a1$ and $\theta a2$ (and $\theta b1$ and $\theta b2$) of the converged light beams Fa1 and Fa2 (and Fb1 and Fb2) onto the object to be measured 1 can be changed by moving the mirror 12 upward and downward, the mirror 12 itself does not need to be replaced and the incident angles can easily be changed.

It should be noted that various variations of an embodiment of the present invention are conceivable.

Figure 2:
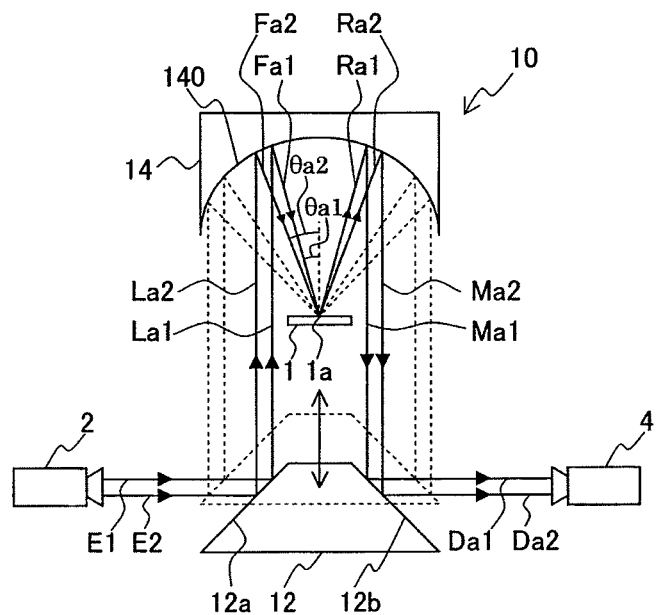
FIG. 2 is a front view showing a configuration of the reflected light measurement device according to a first variation of an embodiment of the present invention, and shows a case where the mirror 12 is moved downward (refer to FIG. 2(*a*)) and a case where the mirror 12 is moved upward (refer to FIG. 2(*b*))
Figure 2:
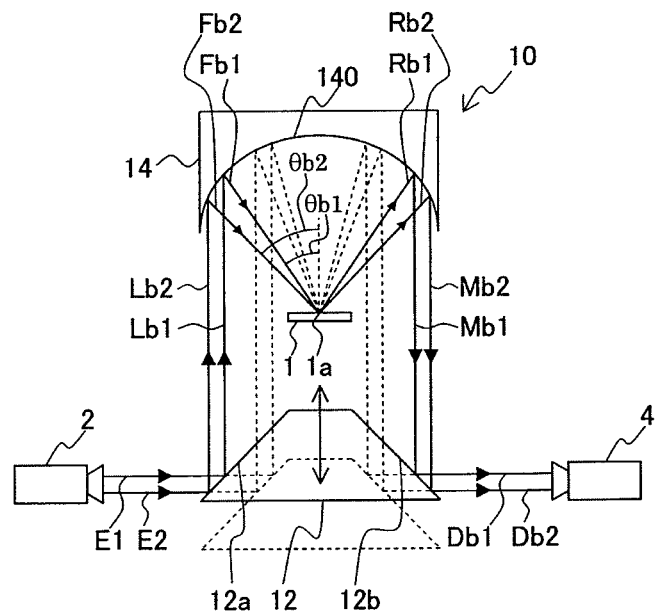

FIG. 2 is a front view showing a configuration of the reflected light measurement device according to a first variation of an embodiment of the present invention, and shows a case where the mirror 12 is moved downward (refer to FIG. 2(a)) and a case where the mirror 12 is moved upward (refer to FIG. 2(b)).

In the reflected light measurement device according to the first variation, the off-axis parabolic mirror (light beam converging device) 14a and the off-axis parabolic mirror (paralleling device) 14b according to an embodiment of the present invention are unified into an off-axis parabolic mirror 14. The off-axis parabolic mirror 14 includes a reflective parabolic surface 140. The parallel light beams La1 and La2 (and Lb1 and Lb2) hit on and are reflected by the reflective parabolic surface 140 (refer to the converged light beams Fa1 and Fa2 (and Fb1 and Fb2)). The reflected light beams Ra1 and Ra2 (and Rb1 and Rb2) hit on and are reflected by the reflective parabolic surface 140 (refer to the reflected parallel light beams Ma1 and Ma2 (and Mb1 and Mb2)). It should be noted that the one point 1a on the surface of the object to be measured 1 is arranged at the focal point of the reflective parabolic surface 140.

Figure 3:
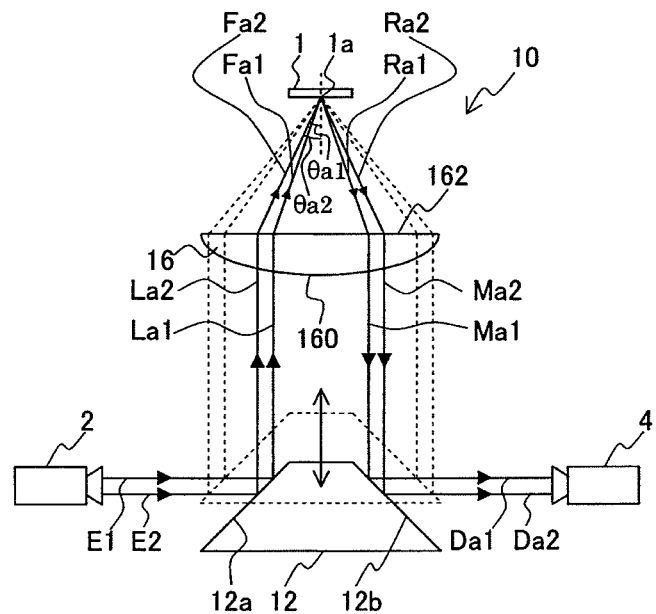
FIG. 3 is a front view showing a configuration of the reflected light measurement device according to a second variation of an embodiment of the present invention, and shows a case where the mirror 12 is moved downward (refer to FIG. 3(a)) and a case where the mirror 12 is moved upward (refer to FIG. 3(b))
Figure 3:
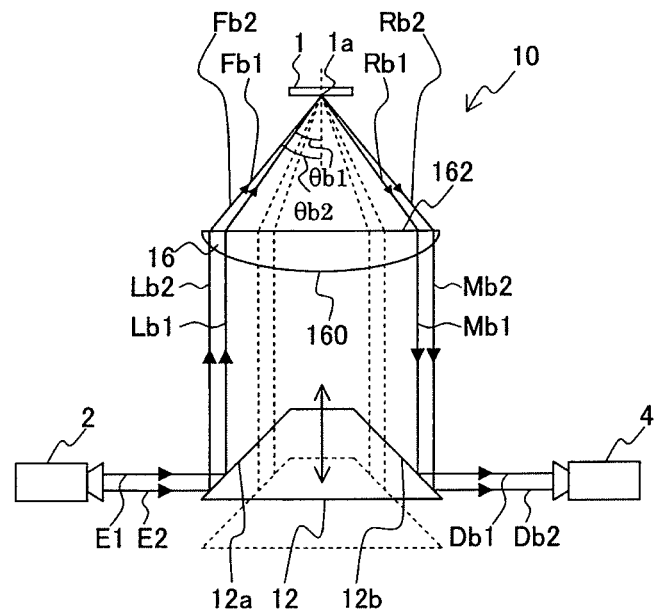
Figure 4:
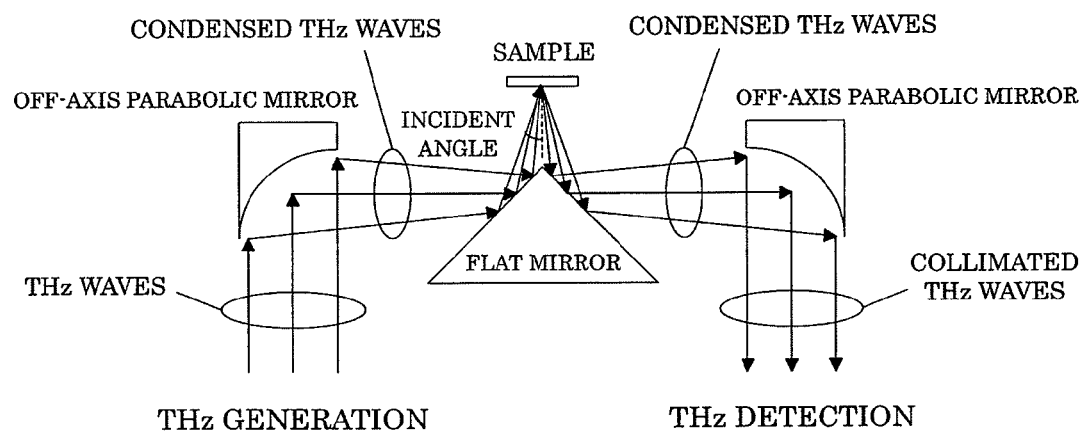
FIG. 4 shows an optical system of a conventional reflection measurement device which measures optical characteristics of a flat-shape sample.

FIG. 3 is a front view showing a configuration of the reflected light measurement device according to a second variation of an embodiment of the present invention, and shows a case where the mirror 12 is moved downward (refer to FIG. 3(a)) and a case where the mirror 12 is moved upward (refer to FIG. 3(b)).

Although the beam converging device and the paralleling device are unified into the off-axis parabolic mirror 14 according to the first variation, the unified devices are not limited thereto. The light beam converging device and the paralleling device are unified into an aspherical lens 16 in the reflected light measurement device according to the second variation.

The aspherical lens 16 includes an aspherical curved surface 160 and a flat surface 162. The aspherical lens 16 is arranged between the object to be measured 1 and the mirror 12. The aspherical curved surface 160 is arranged on the mirror 12 side, and the flat surface 162 is arranged on a side of the one point 1a on the surface of the object to be measured 1. The one point 1a on the surface of the object to be measured 1 is arranged at the focal point of the aspherical lens 16.

Although refraction on the aspherical curved surface 160 is not shown in FIG. 3, refraction actually occurs.

Referring to FIG. 3(a), the aspherical lens 16 receives and refracts the parallel light beams La1 and La2 at a portion on the left side with respect to the center of the aspherical curved surface 160, and converges the parallel light beams La1 and La2 at the one point 1a on the surface of the object to be measured 1 (refer to the converged light beams Fa1 and Fa2).

The converged light beams Fa1 and Fa2 are reflected at the one point 1a on the surface of the object to be measured 1 (refer to the reflected light beams Ra1 and Ra2).

Further, the aspherical lens 16 receives and refracts the reflected light beams Ra1 and Ra2 at a portion on the right side with respect to the center of the flat surface 162, thereby obtaining light beams traveling in parallel (refer to reflected parallel light beams Ma1 and Ma2).

Referring to FIG. 3(b), the aspherical lens 16 receives and refracts the parallel light beams Lb1 and Lb2 at a portion on the left end of the aspherical curved surface 160, and converges the parallel light beams Lb1 and Lb2 at the one point 1a on the surface of the object to be measured 1 (refer to converged light beams Fb1 and Fb2).

The converged light beams Fb1 and Fb2 are reflected at the one point 1a on the surface of the object to be measured 1 (refer to the reflected light beams Rb1 and Rb2).

Further, the aspherical lens 16 receives and refracts the reflected light beams Rb1 and Rb2 at a portion on the right end of the flat surface 162, thereby obtaining light beams traveling in parallel (refer to the reflected parallel light beams Mb1 and Mb2).

Even if the light converging device and the paralleling device are unified into the aspherical lens 16 as in the second variation, the same effects can be achieved as in the above-described embodiment of the present invention.

The invention claimed is:

1. A light beam incident device comprising:
a light beam converging device that receives parallel light beams, and converges the parallel light beams at one point on an object to be measured; and
a light beam feeding device that is positioned farther from a top portion of the light beam converging device than the object to be measured, and feeds the parallel light beams to the light beam converging device, wherein:
the light beam feeding device receives incident light beams travelling in parallel and changes a travel direction of the incident light beams by a right angle, to feed the parallel light beams to the light beam converging device,
the light beam converging device changes an angle between the object to be measured and converged light beams obtained by converging the parallel light beams, in accordance with a light reception position at which the light beam converging device receives the parallel light beams;
the light beam feeding device moves parallel to an emission direction of the parallel light beams output from the light beam feeding device to the light beam converging device, to change the light reception position on the light beam converging device; and
the object to be measured is positioned between the light beam converging device and the light beam feeding device.

2. The light beam incident device according to claim 1, comprising a paralleling device that changes travel directions of reflected light beams obtained by reflecting the converged light beams at the one point on the object to be measured, to obtain reflected parallel light beams traveling in parallel.

3. The light beam incident device according to claim 2, wherein the light beam converging device and the paralleling device are unified with each other.

4. The light beam incident device according to claim 3, wherein the light beam converging device is one of an off-axis parabolic mirror and an aspherical lens.

5. The light beam incident device according to claim 2, wherein the light beam converging device and the paralleling device are distinct from each other.

6. The light beam incident device according to claim 2, comprising a travel direction changing device that receives the reflected parallel light beams, and changes a travel direction of the reflected parallel light beams by the right angle, to obtain light beams with a changed travel direction.

7. The light beam incident device according to claim 6, wherein:
the travel direction of the incident light beams and the travel direction of the light beams with the changed travel direction are the same.

8. The light beam incident device according to claim 6, wherein the light beam feeding device and the travel direction changing device are unified with each other.

9. A reflected light measurement device comprising:
   the light beam incident device according to claim 1;
   a light source that feeds the incident light beams to the light beam incident device; and
   a detector that detects light beams with a changed travel direction from the light beam incident device.

\* \* \* \* \*